(12) United States Patent
Lee et al.

(10) Patent No.: US 6,486,134 B2
(45) Date of Patent: Nov. 26, 2002

(54) GENE TREATMENT TO ENHANCE FEED EFFICIENCY AND GROWTH RATE OF LIVESTOCK

(75) Inventors: Fuk-ki Lee, Shatin (HK); Kai-Tong Tam, Shatin (HK); Sing-Fai Wai, Shatin (HK)

(73) Assignee: LeaderGene Limited, Shatin (HK)

( * ) Notice: Subject to any disclaimer, the term of this patent is extended or adjusted under 35 U.S.C. 154(b) by 57 days.

(21) Appl. No.: 09/398,473

(22) Filed: Sep. 17, 1999

(65) Prior Publication Data

US 2002/0137701 A1 Sep. 26, 2002

(51) Int. Cl.$^7$ .............................................. H61K 48/00

(52) U.S. Cl. ...................... 514/44; 424/93.2; 435/320.1; 435/69.1; 435/91.4; 435/455

(58) Field of Search ..................... 514/44, 12; 536/23.1, 536/23.51, 24.1; 435/455, 91.4, 320.1, 69.1; 530/399; 424/178.1, 93.2

(56) References Cited

U.S. PATENT DOCUMENTS

| | | | | |
|---|---|---|---|---|
| 5,015,626 A | | 5/1991 | Christian et al. | ............. 514/12 |
| 5,036,045 A | * | 7/1991 | Thorner | ........................ 514/12 |
| 5,134,120 A | | 7/1992 | Boyd et al. | ..................... 514/12 |
| 5,292,721 A | * | 3/1994 | Boyd et al. | ..................... 514/12 |
| 5,298,422 A | * | 3/1994 | Schwartz et al. | ......... 435/320.1 |
| 5,846,936 A | * | 12/1998 | Felix | ............................ 514/12 |

FOREIGN PATENT DOCUMENTS

| EP | 0289186 | | 11/1988 |
|---|---|---|---|
| GB | 2 198 643 | * | 6/1988 |

OTHER PUBLICATIONS

Anderson, W.F. Human Gene Therapy. Nature 392(Supplement):25–30, Apr. 1998.*
Hodgson, C.P. Advances in Vector Systems for Gene Therapy. Exp. Opin. Ther. Patents 5(5):459–468, 1995.*
Miller, N. et al. Targeted Vectors for Gene Therapy. FASEB Journal 9:190–199, 1995.*
Reecy, J.M. et al. Multiple Regions of the Porcine alpha–Skeletal Actin Gene Modulate Muscle–Specific Expression in Cell Culture and Directly Injected Skeletal Muscle. Animal Biotechnology 9(2):101–120, 1998.*
Verma, I.N. Gene Therapy—Promises, Problems and Prospects. Nature 389:239–242, Apr. 1998.*
Draghia–akli et al., Nature Biotechnology 15: 1285–1289, 1997.*
Reecy et al, Gene 180, "Structure and regulation of the porcine skeletal . . . ", pp. 23–28, Apr. 27, 1996.
Holden et al, Porcine somatotropin (pST), pp. 1–6, Aug. 1993.
Draghia–Akli et al, Research, "Enhanced growth by ectopic expression of growth . . . ", pp. 1285–1248, Aug. 20, 1997.
Reecy et al, Animal Biotechnology, 9(2), "Multiple regions of the porcine . . . ", pp. 101–120, 1998.
Ruxandra Draghia–Akli et al, Nature Biotechnology, vol. 17, "Myogenic expression of an . . . ", pp. 1179–1183, Dec. 1999.

* cited by examiner

*Primary Examiner*—Dave T. Nguyen
(74) *Attorney, Agent, or Firm*—Jacobson Holman, PLLC

(57) ABSTRACT

This invention relates to the enhancement of feed efficiency and growth rate, and the reduction of fat accumulation to produce better quality meat by administration of an exogenous gene sequence comprising the complementary DNA sequence of growth hormone releasing factor to stimulate the production of the endogenous hormone peptide growth hormone. This invention further relates to methods for producing such gene sequence.

19 Claims, 8 Drawing Sheets

Effects GHRF Gene Treatment On Mean Back Fat Thickness In Male LY Pigs

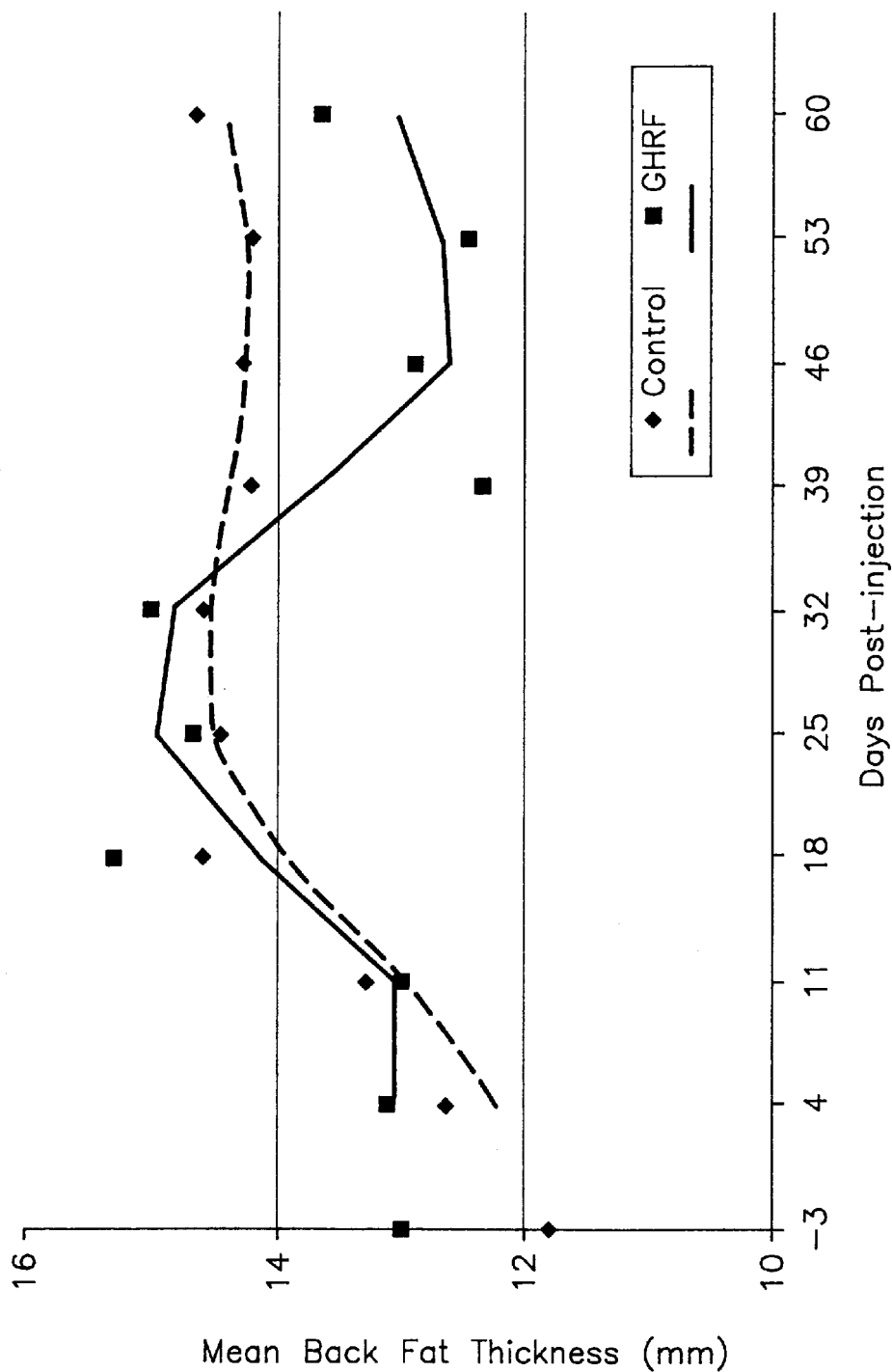

GENE TREATMENT TO ENHANCE FEED EFFICIENCY AND GROWTH RATE OF LIVESTOCK

FIELD OF INVENTION

The present invention relates to the administration of an endogenous hormone peptide, more particularly, to the administration of an endogenous hormone peptide with gene-based material to enhance feed efficiency and growth rate of livestock.

BACKGROUND

There have been many approaches to stimulate the growth rate of livestock and to enhance feed conversion efficiencies. These include the use of antibiotics, chemicals, and the use of biological compounds such as native or recombinant growth hormones (GH) or growth hormone releasing factors (GHRF). Many of these approaches either have side effects or are too expensive to implement in actual farms or ranches.

Although antibiotic supplements have been routinely used to enhance growth performance and feed conversion in the past, their benefits are now diminishing due to improvements in modern farm management and the potential danger of spreading antibiotic resistance to other animals including man.

The earliest attempts in biological enhancement used injections of pituitary extracts, from which the pituitary GH was later isolated and purified.

GH produces a variety of effects on body tissues, ultimately leading to an increase in growth rate and weight gain. In vivo, GH stimulates the synthesis of proteins, the breakdown of fats, and epiphyseal growth. These effects are mediated via the up-regulation of somatomedins, for example insulin-like growth factor I (IGF-I). The production and release of pituitary GH is under the control of two hypothalamic hormone peptides. Inhibition by somatostatin and stimulation by GHRF regulates the plasma GH levels. As animals age, there are deleterious changes in the GHRF→GH→IGF-I axis. Hence in older animals including man, GH production rate decreases, and the IGF-I response to GH and GHRF diminishes. These lead to osteoporosis, decrease of lean muscle, and increasing truncal fat deposits. Therefore pituitary extracted GH has been used to supplement the natural decline in GH and enhance growth. However, such a treatment suffers from the risks of adventitious pathogen transmission. In addition, the major drawback is the high costs involved. Since GH is a protein, it is easily digested by intestinal enzymes and must be administered by injection. Furthermore, GH has to be given daily due to its short serum half-life. This pushes up the cost of treatment, making it feasible only for human therapy.

The development of recombinant DNA technology and the use of microbes such as *E. coli* to produce mammalian GHs meant that homogenous GH preparations could be produced in large quantities for treatment, thereby reducing the costs. Additionally, recent advances in protein stabilization by engineering substitutions in the primary structure and development of slow release formulations have reduced the frequency of dosing to weekly or bi-weekly. As the costs of treatment lower, it can be used commercially to boost agricultural production. For instance, recombinant bovine GH is currently being used to boost milk production in a third of the United States of America dairy herd.

Treatment of pigs with porcine GH was shown to enhance growth rate, increase carcass protein whilst reducing the proportion of fat. The benefits of porcine GH on pig's growth performance and the safety and economic aspects involved have been reviewed by Palmer J. Holden (Porcine somatotropin (pST), Biotechnology Information Series (Bio-4), Iowa State University, 1993). Summarizing data from twenty studies, it was reported that porcine GH injected pigs grow 15% faster whilst consuming 21% less feed, with more muscle protein and reduced backfat. However, these gains in productivity are made at substantial costs. Firstly, because of its short serum half-life and rapid clearance from the bloodstream, GH must be injected daily to be effective. Hence pigs must be given up to 4 mg of porcine GH protein per day for the one or two month duration of the finishing period to sustain plasma GH levels and improve growth performance. Thus each pig may eventually require as much as 400 mg of GH. Secondly, high doses may be toxic and have been shown to cause some adverse side effects such as breathing difficulties, as described in the U.S. Pat. No. 5,134,120. Moreover, the treatment regiment so far described in the literature is too labor intensive and traumatic to the animal. Even though U.S. Pat. Nos. 5,015,626 and 5,134,120 describe the use of porcine GH to improve meat quality and enhance weight gain respectively, the current technology in GH peptide-based growth promotants are yet to be economical to apply to commercial farming.

The discovery of the growth hormone releasing factors (GHRF) promised to provide a better method of growth enhancement. GHRF is a peptide hormone secreted by the hypothalamus and specifically stimulates the synthesis and release of GH by the somatotroph cells of the anterior pituitary gland. By stimulating the endogenous production of GH, the effective dose required is much smaller than that of GH, thus providing a more physiologic mode of treatment at potentially lower costs. Nevertheless, to the best of our knowledge, there appears to be still no satisfactory and cost effective treatment for livestock. For example, the use of human GHRF protein injections twice daily to stimulate the growth of sheep was described in EP Pat. No. 0,289,186. However, prolonged injections of the human GHRF induce immune response in sheep with neutralizing antibody formation against the human protein. This lowers the efficiency of such a treatment, and the labor and material costs render this approach uneconomical. Injections of GHRF peptide have been used to produce a more sustained stimulation of production of GH in the pig. Although some trials have shown success in producing a gain in body weight and lower carcass fat content, the same problem of rapid clearance means frequent doses are required. Therefore a new approach to supplement GH levels for growth enhancement is required.

Since it was first demonstrated that intramuscular-injected plasmid DNA vectors are taken up by the skeletal muscle cells and expressed for many months in vivo, skeletal muscle based gene therapy has held great promise for the systemic delivery of therapeutic proteins. This skeletal muscle production of recombinant proteins which can be secreted into the circulation system to reach distant target sites ideally suites the treatment of diseases arising from serum protein deficiencies. Plasmid vectors, although much less efficient in protein expression than viral based vectors, have the advantages of being less likely to be immunogenic and not integrated into the host genome. Therefore, they are generally thought to be safer. On this basis plasmid vectors best suit situations where the therapeutic protein is effective at low concentrations. Thus, injection of plasmid vectors expressing the gene for GHRF may be an ideal method to apply a chronic supplement of GHRF at an effective dose sufficient to enhance growth performance of animals. Furthermore, persistent GHRF production should drastically reduce the frequency of treatment, hence lowering the costs to an economically viable level.

Recently, it was shown that a plasmid containing human GHRF (hGHRF) cDNA under the control of the chicken minimal skeletal α-actin promoter is able to produce an elevation in plasma GH levels when injected into the mouse muscle (Draghia-Akli et al, Nature Biotechnology, 15, p1285–1289). Furthermore, growth enhancement of approximately 15% was reported at 3 weeks post injection. However, their methods elicited an immune response as evidenced by the increasing serum levels of neutralizing anti-hGHRF antibodies at 21 and 28 days after hGHRF gene injection. It has been shown that the limiting factor in the level of in situ gene expression from injected plasmids is the extremely low degree of uptake of plasmid DNA by the muscle fibers. To improve the level of hGHRF expression, Draghia-Akli and co-workers first injected bupivacaine, a well known myotoxic substance, before injecting the plasmid DNA into the regenerating muscle. Although this has been shown to improve the level of expression by increasing plasmid uptake in the muscle fibers, it is neither a desirable nor an acceptable technique to apply in farm animals reared for human consumption.

OBJECT OF THE INVENTION

It is therefore an object of this invention to provide a cost-effective approach to stimulate the growth rate of animals, particularly livestock animals, and to enhance feed conversion efficiencies through the administration of an endogenous hormone peptide GHRF. As a minimum, it is an object of the present invention to provide the public with a useful choice.

SUMMARY OF THE INVENTION

Accordingly, there is provided a method of enhancing feed efficiencies and/or growth rates and/or reducing fat accumulation of animals comprising administration of endogenous hormone peptide GHRF by an exogenous gene sequence to stimulate the production of GHRF, and said exogenous gene sequence comprises a DNA sequence encoding a promoter for gene expression, a complementary DNA (cDNA) sequence encoding a GHRF signal peptide, and a cDNA sequence encoding GHRF.

Among the particularly preferred embodiments of this invention are variants of the promoter being an actin promoter. In accordance with certain preferred embodiments of this invention, the actin promoter is a skeletal actin promoter. The DNA sequence encoding a skeletal actin promoter particularly prefers comprising a full set of DNA sequence of the skeletal actin promoter.

In accordance with another preferred embodiments of this invention, the exogenous gene sequence further includes a DNA sequence encoding the three prime (3') untranslated polyadenylation signal-containing region of the gene of the promoter or GHRF.

In accordance with yet another preferred embodiments of this invention, the exogenous gene sequence further includes a DNA sequence encoding a gene for antibiotic resistance.

The GHRF and its signal peptide encoded by said cDNA sequences can be the corresponding natural or recombinant or synthetic, or biologically active fragments or their analogues with similar activities. It is a particularly preferred embodiment of this invention that the DNA sequence of the promoter, the cDNA sequence encoding a GHRF signal peptide, and the cDNA sequence encoding GHRF are species specific.

The said exogenous means to stimulate the production of GHRF being a DNA sequence is preferably mixed with a suitable carrier to be administered subcutaneouly. In accordance with certain preferred embodiments of this invention, the exogenous DNA sequence is administered via intramuscular route.

The said exogenous means to stimulate the production of GHRF being a DNA sequence given per animal is preferably between the range of 1 to 100 μg per kg body weight of the animal.

It is another aspect of this invention to provide an exogenous gene sequence to simulate the endogenous production of GHRF to enhance feed efficiencies and/or growth rates and/or reduce fat accumulation of animals, wherein the exogenous gene sequence comprise a DNA sequence encoding an promoter for gene expression, a cDNA sequence encoding a GHRF signal peptide, and a complementary DNA (cDNA) sequence encoding GHRF.

It is yet another aspect of this invention to provide a method of manufacturing a medicament to enhance the feed efficiencies and/or growth rates and/or reduce fat accumulation of animals comprises providing a DNA sequence encoding a promoter for gene expression, joining a cDNA sequence encoding a GHRF signal peptide, and joining a cDNA sequence encoding GHRF to form a gene sequence and mixing said peptide with a suitable carrier.

Other objects, features, advantages, and aspects of the present invention will become apparent to those skilled from the following description. It should be understood, however, that the following description and the specific examples, while indication preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE FIGURES

A preferred embodiment of the present invention will now be explained by way of example and with reference to the accompanying figures in which:

FIGS. 7a and 7b show the change in mean back-fat thickness in the Landrace/Yorkshire pigs after pGHRF gene injection.

DETAILED DESCRIPTION OF THE PREFERRED EMBODIMENT

Figure 1:
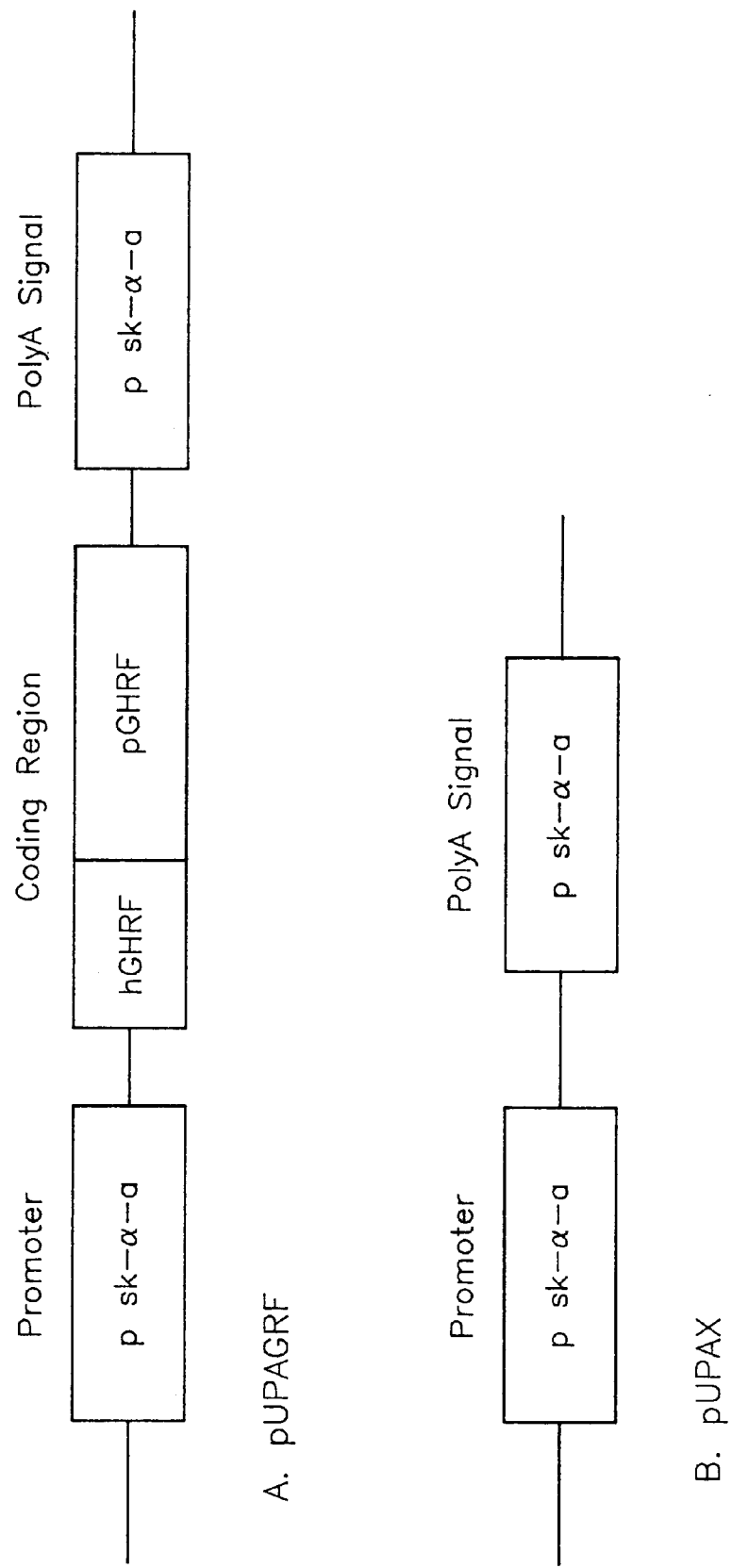
FIG. 1 shows the schematic representations of pUPAGRF, the pGHRF expression cassette, with the arrangement of the promoter, pGHRF coding region and polyadenylation signal, while the control plasmid pUPAX is produced by deleting the pGHRF coding region.

Preferably, the muscle specific GHRF expression system is constructed in a plasmid vector. The complementary DNA (cDNA) sequences encoding GHRF signal peptide and GHRF itself were designed from the published peptide primary structure and optimized for mammalian codon usage. This cDNA is synthesized using conventional oligonucleotide synthesis chemistry. The GHRF and its signal peptide encoded by the cDNA sequences can be the corresponding natural or recombinant or synthetic, or biologically active fragments or their analogues with similar activities. The GHRF leader sequence encodes a signal peptide in the nascent GHRF peptides that will direct the export of said GHRF peptides out of the muscle cells and secretion into the general circulation in an active form.

The DNA sequences for promoter/enhancer elements and the three prime (3') untranslated, polyadenylation signal containing regions of the promoter/GHRF gene is separately cloned by polymerase chain reaction. As an example, the skeletal α-actin (skαa) promoter/enhancer is used, but this should not be considered as a restriction to the choice of promoter/enhancer. The full set of, but not a minimal subset of such an actin promoter as described by Draghia-Akli et al, is used. The reason is that in vivo studies using direct gene injection have shown that the full skeletal α-actin promoter gave the highest level of gene expression in the mouse muscle when compared to other truncated versions (Reecy et al., Animal Biotechnology 2: 101–120, 1998).

As a preferred embodiment of this invention, the DNA sequences of the actin promoter, the cDNA sequence encoding a GHRF signal peptide, and the cDNA sequence encoding GHRF are species specific.

These segments of DNA are inserted into a pUC plasmid in the following order: actin promoter; human GHRF signal peptide cDNA: porcine GHRF (1–44) cDNA; actin 3' untranslated region. The pUC plasmid also contains a gene for antibiotic resistance, for instance ampicillin resistance, that allows selection when transformed into E. coli bacteria, as well as a ColEI origin of replication that confers high plasmid copy number.

E. coli transformed with the GHRF expression plasmid is then grown in a fermenter under ampicillin selection. After harvesting the cells and release of plasmids by alkaline lysis, the plasmid DNA is separated from the RNA, the bacterial DNA and other cellular contaminants by column chromatography. The integrity of the purified plasmid DNA is verified by restriction enzyme digestion/agarose gel electrophoresis and DNA sequencing. Purity is determined by measuring absorbance at $OD_{260/280}$ and agarose gel electrophoresis.

Assayed plasmid DNA is dissolved in a physiologically acceptable carrier, tested for pyrogen levels, dose adjusted and administered to animals via intramuscular injection. As a preferred embodiment of this invention, the total amount of said plasmid DNA given per animal should be between the range of 1 to 100 µg per kg body weight of the livestock.

Upon injection into the muscle of the animals, the plasmid expression vector, being a DNA, is taken up into the muscle cells. The plasmid expression vector will then direct the cell to produce GHRF peptides. Such peptides are released into the circulation system and stimulates the production of GH on reaching the pituitary gland. This results in the elevation of GH in the circulation system that improves growth performance, results in faster growth rate, higher lean-body mass and better food conversion. Furthermore, the meat produced is leaner and with less fat, hence of a higher market value.

Furthermore, the normal negative feedback control of GH via the hormone somatostatin is bypassed, as GHRF release is under the control of a constitutive muscle specific promoter. This allows the continuous production of GH.

The following examples are offered to further illustrate but not limit the embodiments of the present invention.

EXAMPLE 1

Construction of the pGHRF Expression Plasmid Vector

The pGHRF expression construct was designed to give optimal production and secretion of the pGHRF peptide when transfected into mammalian muscle cells (FIG. 1).

Skeletal alpha-actin (skαA) promoter is a well characterized promoter that has been shown to give highly specific gene expression in differentiated muscle fiber cells (Reecy et al, Gene 180: 23–26 1996). Furthermore, it possesses a high degree of sequence identity and share many transcription factor consensus binding site comparing with the human, bovine and chicken skαa promoters. This suggests that this promoter is highly conserved between mammals and birds. This is supported by in vitro studies demonstrating the ability of the porcine skαa promoter to confer muscle specific gene expression in mouse, rat and porcine cells. Hence this 2 kb promoter was chosen to drive the muscle specific expression of the pGHRF cDNA.

The porcine skαa promoter was spliced in front of an open reading frame that comprises the DNA sequence coding for the human GHRF signal peptide and the porcine GHRF mature peptide.

Figure 2:
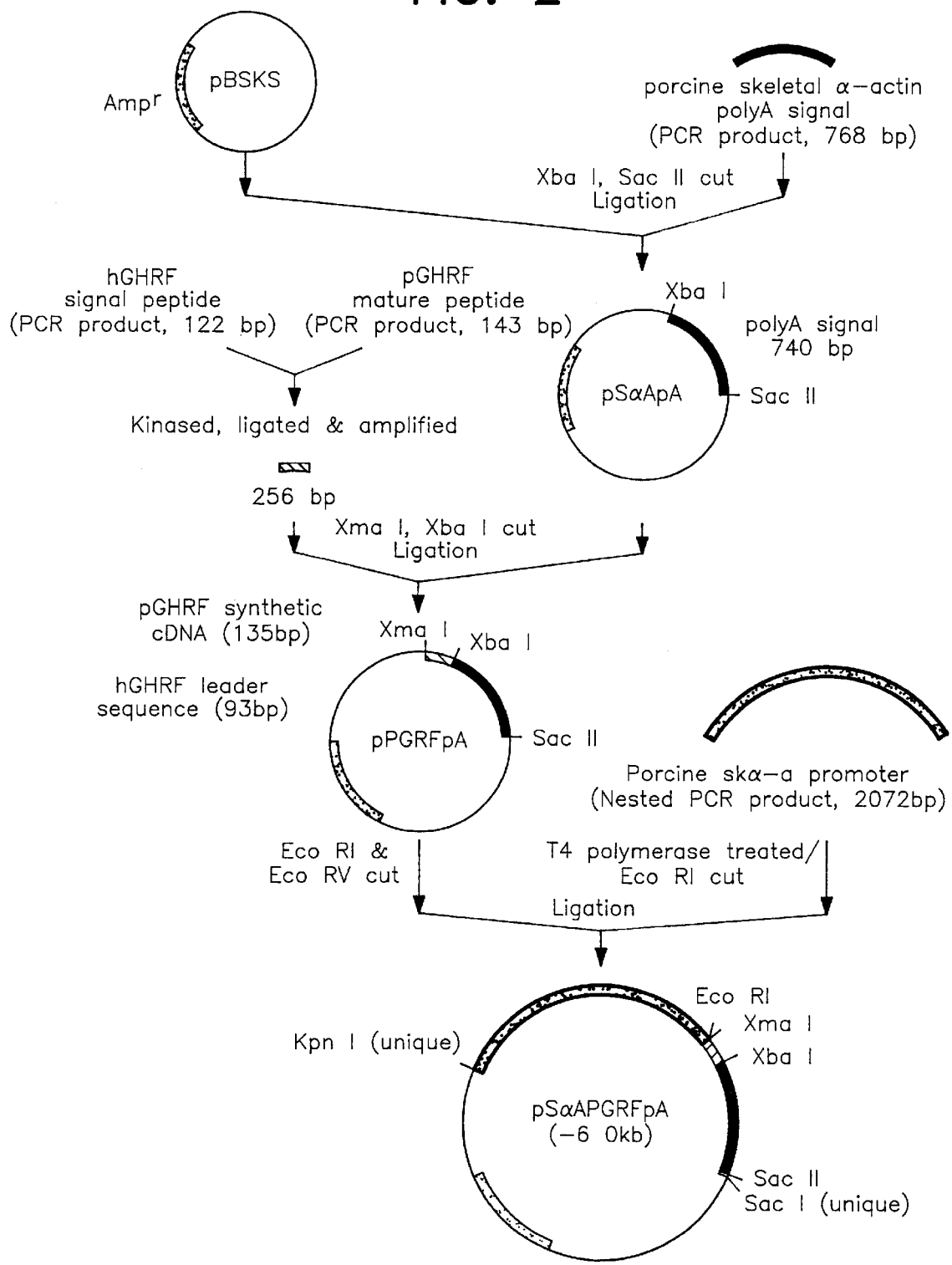
FIG. 2 shows the major steps involved in the construction of pUPAGRF plasmid giving the key enzymes used.

Since the DNA sequence encoding porcine GHRF was not available, we designed this by reverse translation of the known peptide structure, with optimization for mammalian codon preference. A further modification of the present invention involves the addition of the 3' untranslated region of the porcine skeletal α-actin gene downstream of the coding region. This serves to enhance expression of the pGHRF product by stabilizing and prolonging the half-life of the mRNA transcripts. The method of construction for the pGHRF expressing plasmid is detailed below and summarized in FIG. 2.

PolyA region: Genomic DNA was purified from porcine kidney and used for amplification of porcine gene sequences. A 750 bp 3' end fragment of the skαa gene was amplified by PCR. This region spans nucleotide number 2464 to 3204 of the published sequence (Genbank Accession No. U16368) and contains the 3' untranslated region and putative polyadenylation signal. The product was then cut with restriction enzymes Xba I and Sac II (using cuts sites introduced with the PCR primers) and cloned into plasmid vector pBluescript KS+ to get pSαApA.

GHRF coding region: The GHRF coding region is an open reading frame (ORF) that comprises the DNA "leader sequence" encoding a signal peptide for human GHRF succeeded by an inframe porcine GHRF (1–44) cDNA. The leader sequence, containing full exon 2 and partial exon 3 of the human GHRF gene (Genbank Accession No. L10034-5) was PCR amplified from human genomic DNA. The porcine GHRF cDNA was constructed as two oligonucleotides with the following sequences:

LGPGRF1 5'-TACGCCGACGCCATCTTCACC AACAGCTACAGGAAGGTGCGGCCAGCT- GAGCGCCAGGAAGCTGCTGCAGGACATCATG (SEQ ID NO: 1)

LGPGRF2 5'-CGTCTAGATCACAGCCTCACCCT GGCGCCCTGCTCCTGGT TCCTCTCGCCCTGCT GCCTGCTCATGATGTCCTGCAGCAGC (SEQ ID NO: 2)

These oligonucleotides contained an overlap that was used to anneal them to each other and then filled in with Vent Polymerase. The annealed product was then PCR amplified with Vent Polymerase. The products of the leader sequence and porcine GHRF cDNA were each kinased with T4 polynucleotide kinase and then purified by polyacrylamide gel electrophoresis. Then the products were joined together with T4 DNA ligase and the ligation product of 265 bp further purified using polyacrylamide gel. This ORF product was then re-amplified by PCR with primers containing Xma I and Xba I restriction enzyme sites. The ORF was then cut with Xma I and Xba I enzymes and purified to get a 245 bp fragment. This fragment was then cloned into pSαApA to get pPGRFpA.

Promoter region: The full 2 kb porcine skeletal α-actin (skαa) promoter/enhancer was PCR amplified from porcine genomic DNA. Nested-polymerase chain reaction (PCR) was then done on 1/50 of the first PCR reaction to yield a DNA product that spans bp −1909 to +76 of the porcine skαa gene (Reecy et al, Gene 180:23–28, 1996). This product was blunt-ended with T4 DNA polymerase and then cut with Eco RI. The gel-purified promoter fragment was cloned into the Eco RI and Eco RV sites of pPGRFpA to get the intermediate construct pSαAPGRFpA.

Figure 3:
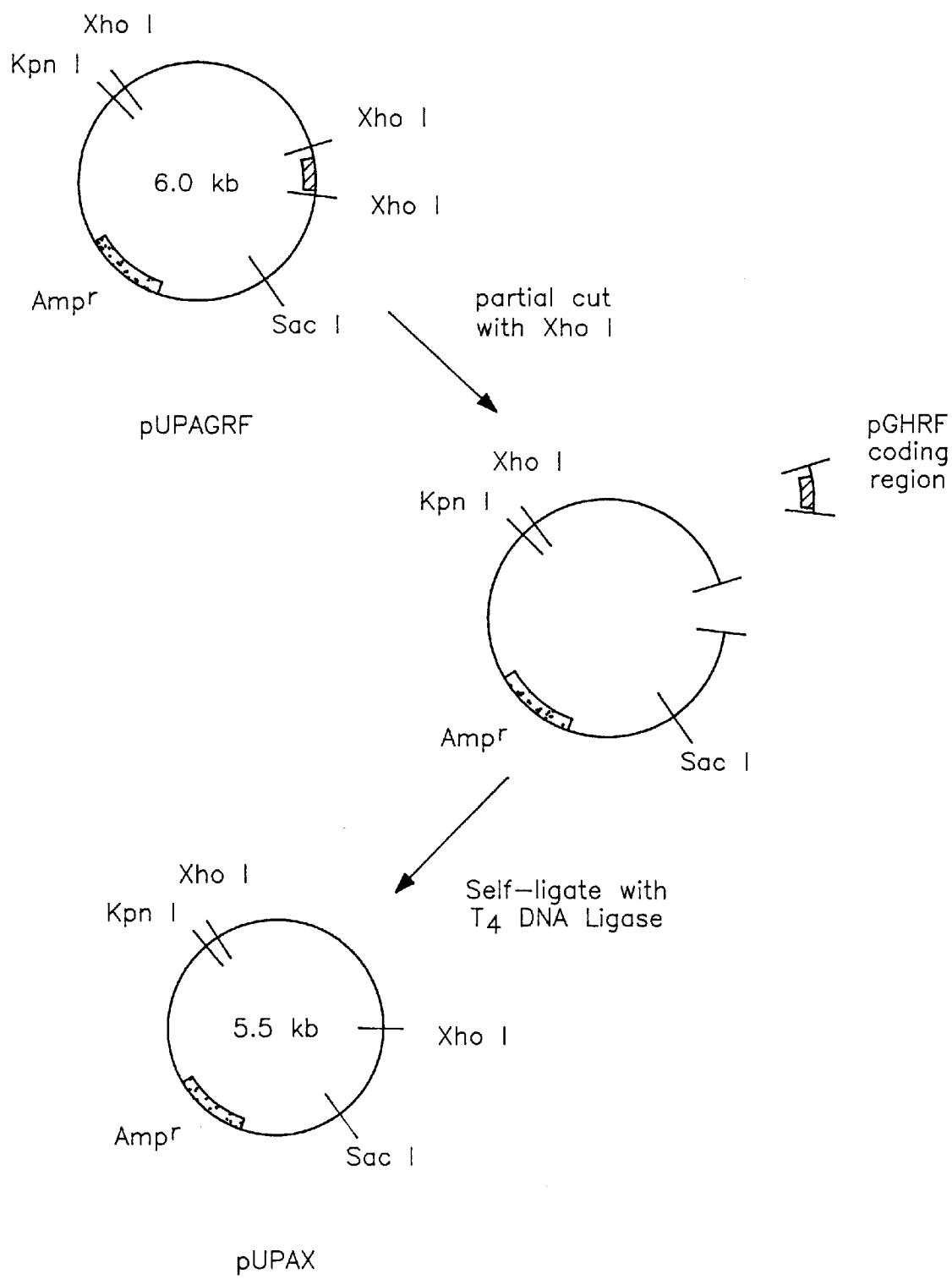
FIG. 3 shows the schematic diagram showing the construction of pUPAX plasmid from pUPAGRF.

To obtain the final construct, this expression cassette was then excised with flanking Kpn I and Sac I restriction enzymes and ligated to plasmid pUC19, and designated pUPAGRF. A second construct was made by removing the entire pGHRF coding region from plasmid pUPAGRF by partial digest with Xho I (FIG. 3). This second plasmid, pUPAX, was used as a control in the animal trials.

The plasmids were separately transformed into *E. coli* K-12 (strain DH5α) and grown in a fermenter using culture media supplemented with 150 μg/ml ampicillin. When the culture reached stationary phase, the bacterial cells were harvested and lysed by classical alkaline lysis. The plasmids were recovered by centrifugation and separated from contaminating cellular DNA, RNA and proteins by anion exchange chromatography. The purity was assayed by measuring the absorbance at 260 and 280 nm. The purified plasmid DNA was also checked for integrity by agarose gel electrophoresis. Finally, identity was confirmed by restriction enzyme digestion and DNA sequencing.

The plasmid DNA was precipitated and redissolved in pyrogen free phosphate buffered saline (PBS) and concentration calculated by taking the absorbance at 260 nm. After passing pyrogen tests, the DNA was ready for animal injection at this point.

EXAMPLE 2

To test the ability of the pUPAGRF construct to enhance growth performance, we injected this plasmid in the quadriceps muscle of the mouse.

From a breeding colony of C57BL/6J mice, forty-eight male mice of 14.5–18 g body weight were selected and randomly assigned to four groups of twelve. Each group of 12 mice were given a single injection of 100 μl PBS containing either 100 μg of control plasmid, or GHRF expression plasmid (pUPAGRF) at 30, 100 or 200 μg, respectively. The mice were weighed, toe-marked for identification, then given a single injection in the middle of the left quadriceps muscle. The mice were kept on a 12 hour daylight cycle under a controlled climate, minimal disease environment and given standard rat chow and water. Body weights were recorded twice per week. The mice were anesthetized with ketamine/xylazine (0.15 ml per 100 g body weight) to obtain blood and tissue samples. Blood was collected by cardiac puncture into a 1 ml insulin syringe containing 30 μl of 0.5 M EDTA as anti-coagulant. Collected blood was kept in ice until plasma was obtained by pelleting the cells at 6000 g for 10 min. The entire quadriceps muscle, which included the injection site was dissected out and snap frozen in liquid nitrogen. The right lobe of the liver was also dissected and immediately frozen. All samples were stored at −80° C. until further analyzed.

Results

Figure 4:
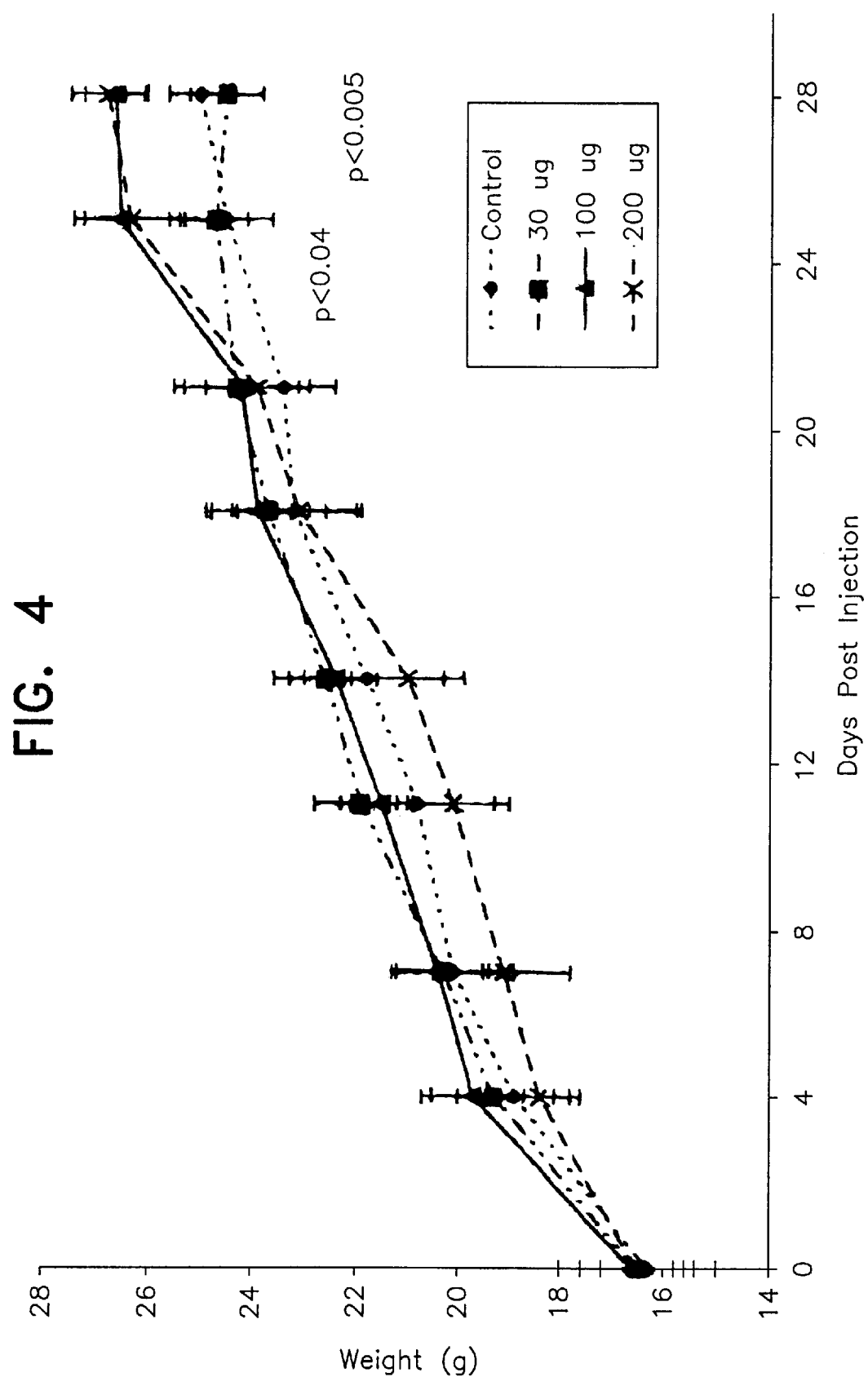
FIG. 4 shows the effects of pGHRF gene injection in the mean body-weight of male C57BL/6J mice over a four-week period on four treatment groups, pUPAGRF plasmid at doses of 30, 100, and 200 μl, or 100 μl of pUPAX control, with injection and weighing performed at 2:00 to 4:00 pm.

Mice in all four treatment groups showed rapid growth and increase in body weight in the four week period after injection. In the 21 day period post injection (P. I), body weight values were not significantly different between all groups. Although mice given 30 μg pUPAGRF showed the highest gain in weight whilst the highest dose (200 μg) group lagged behind (FIG. 4), by 25 days P. I., there were significant differences between the higher doses and the control. At 25 days P. I., mean body weights for the 200, 100 and 30 μg groups were 26.3, 26.5, and 24.7 g, respectively, whilst that for the control group was 24.5 g ($p<0.032$, single factor ANOVA). Mean body weights at 28 days P. I. were 26.8 and 26.6 g for the 200 and 100 μg treated mice, versus 24.5 and 25.0 g for the 30 μg and control treated, respectively. Again, there is significant difference to the weights of the control treated mice ($p<0.0045$).

Figure 5:
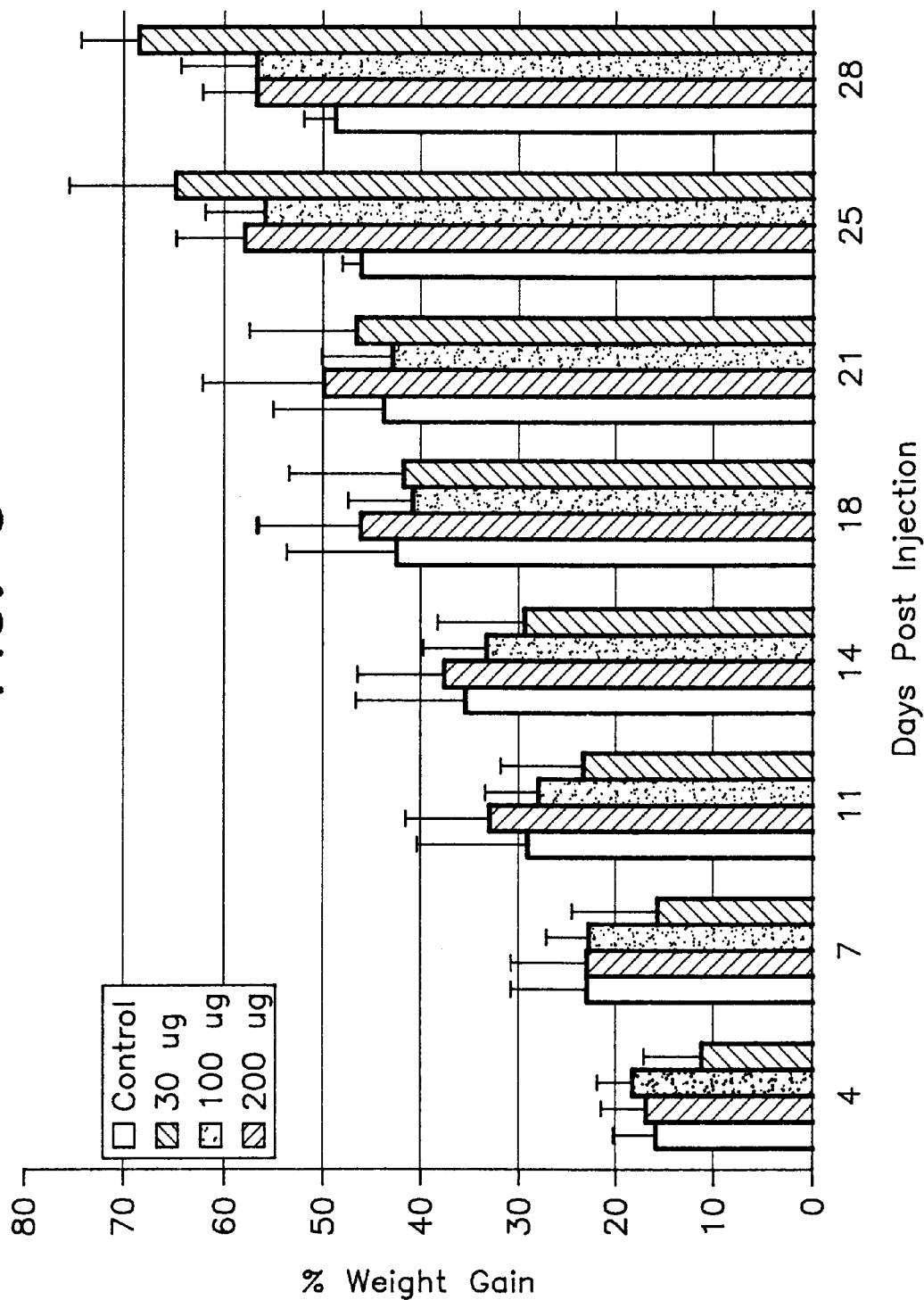
FIG. 5 shows the difference in percentage weight gain of mice injected with the pGHRF gene.
Figure 6:
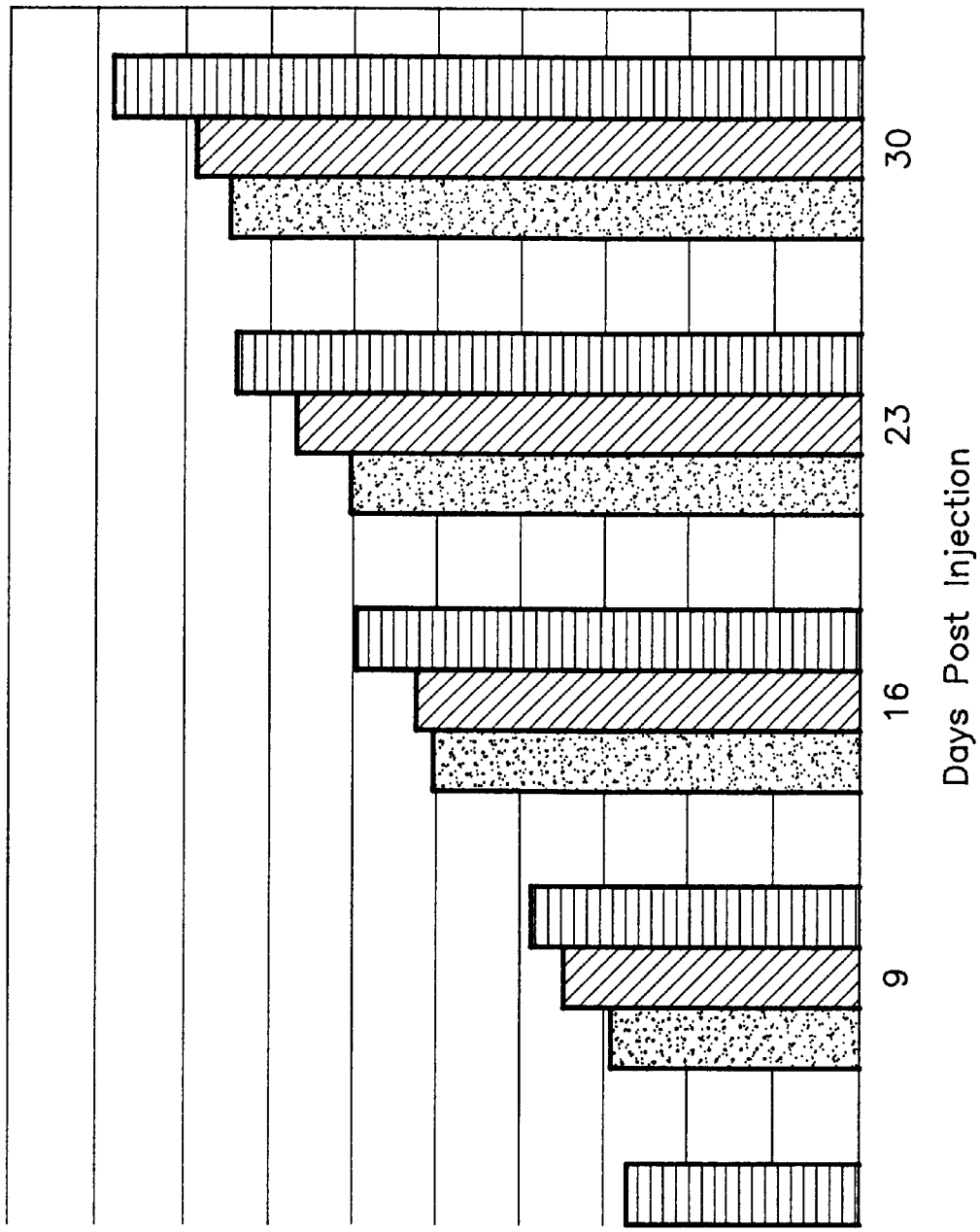
FIG. 6 shows the effects of pGHRF gene dosage on the weight gain in the male Landrace/Yorkshire/Duroc (LYD) pig.

The effects of the pUPAGRF injections on the percentage weight gain are shown in FIG. 5. Four weeks after plasmid injections, control treated mice showed percentage gain of 48.7%, those at 30 and 100 μg of pUPAGRF of 56.6% while those at 200 μg of 68.4%. These results indicate that a single injection of a pGHRF producing plasmid is able to produce a significant improvement in the growth rate of young mice. At doses up to 100 μg, there was an improvement of approximately 8% whilst a dose of 200 μg was able to give a 19% improvement in the percentage weight gain. These results are comparable to the observations of Draghia-Akli in the regenerating mouse muscle, while their injection methods required a prior injection of the myotoxic bupivacaine to enhance plasmid uptake and expression.

EXAMPLE 3

We then tested the ability of the pGHRF gene treatment to improve growth performance in farmed pigs.

Breeder pigs of a triple cross from Landrace/Yorkshire/Duroc (LYD) were used in this study. Young male pigs were randomly assigned into three adjacent pens on a breeder farm at 10 weeks of age. Pigs were given the plasmid preparation by a single injection in the gluteus muscle with a 1½ inch 16 gauge syringe. Pigs in pen A and B were injected with 1 mg and 4 mg of pUPAGRF respectively, while those in pen C were given 4 mg of the control plasmid pUPAX. The pigs were given feed and water ad libitum and weighed weekly.

Results

Pigs given a single injection of 1 mg of pUPAGRF showed a weight gain from 62.53 to 87.17 kg (increase of 37.8%) in the 6 weeks period of the experiment. Pigs injected with 4 mg grown from mean weight of 60.20 kg to 98.28 kg (gain of 44.1%). Those in the control group grown from 58.59 to 89.33 kg (a 34.4% gain) in the same period. Thus after 6 weeks, those pigs injected with a pGHRF expression plasmid showed a higher percentage weight gain than those injected with the control plasmid. Furthermore, there seems to be a trend for a dose dependent response since the 4 mg dose caused over two-fold improvement compared to the 1 mg dose. In terms of feed conversion efficiency, the 1 mg dose group, although showing a modest gain in growth rate, consumed 10% less feed (table 1). Moreover, there was no difference in the amount of feed consumed between the control and high dose group, hence pUPAGRF at both 1 mg and 4 mg doses were able to give an improvement in feed conversion.

TABLE 1

Mean daily feed consumption in the LYD pigs after plasmid injection.

|  | control | 1 mg | 4 mg |
|---|---|---|---|
| mean daily feed consumption per pig (kg) | 3.960 | 3.563 | 3.963 |
| % of control | 100.00 | 89.98 | 100.08 |
| % change relative to control | 0.00 | −10.02 | 0.08 |

EXAMPLE 4

Studies were conducted to determine the effects of injecting 2 mg of pUPAGRF plasmid to Landrace/Yorkshire (LY) pigs on the accumulation of back-fat. Twenty LY pigs at approximately 32 weeks old and average weight of 55 kg were assigned to two groups of ten, each with 5 males and 5 females. One group was administered 2 mg of pUPAGRF plasmid by intramuscular injection. The second group was similarly treated with the plasmid, pUPAX, and served as a control. Back-fat thickness at positions lateral to the last thoracic vertebra was determined weekly using a Renco ultrasound meter. Three measurements were taken at positions PI, PII, and PIII being 45 mm, 65 mm, and 80 mm lateral to the center of the spine at the last rib vertebra respectively, and averaged to give a mean back fat thickness.

Results

Figure 7A:
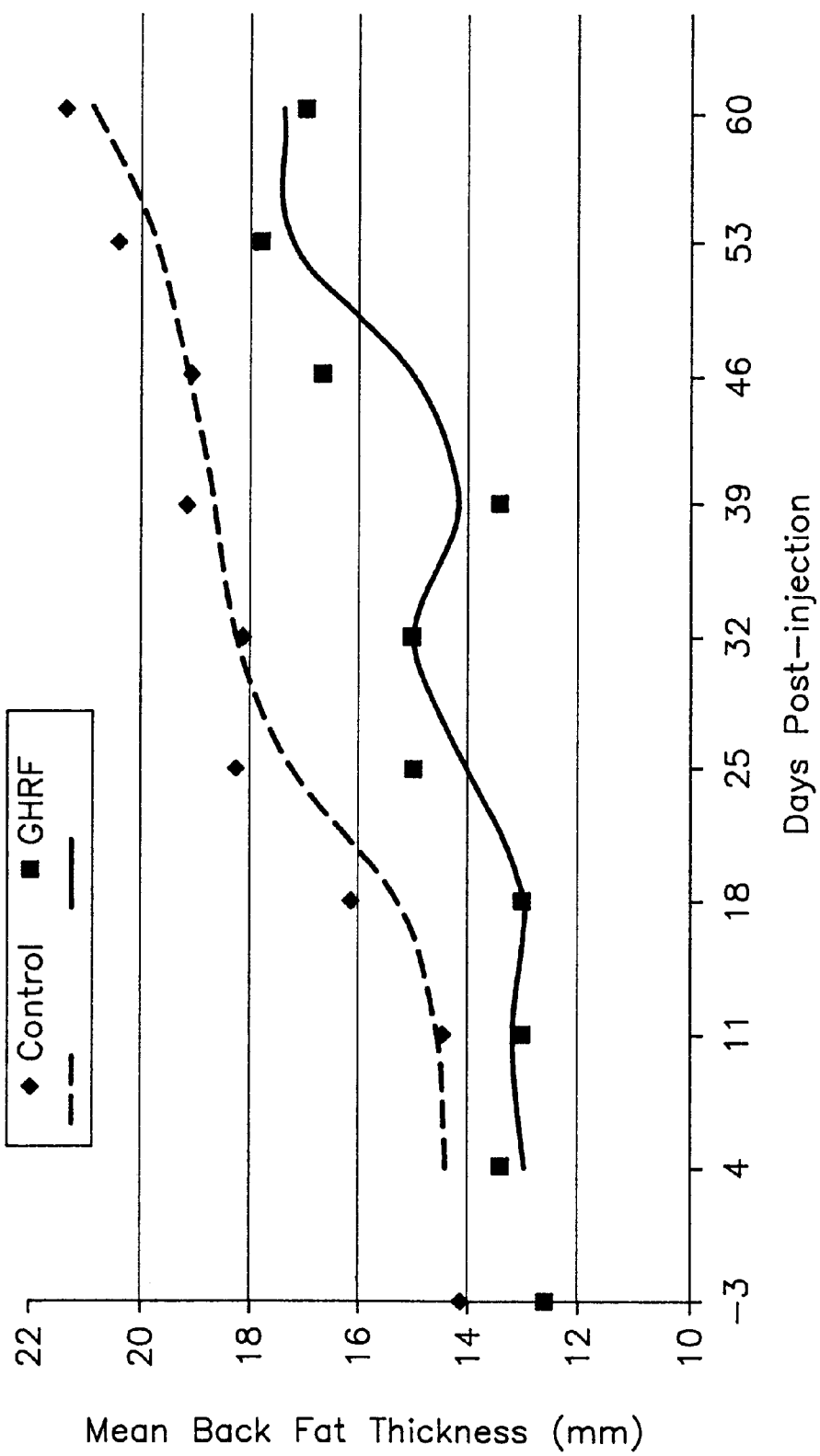

The results are summarized in FIG. 7. In males, both pGHRF treated and control pigs showed gradual increases in back-fat, which is suppressed by pGHRF treatment. Table 2 shows the relative gains in back fat thickness over the experimental period. At 60 days post injection, pGHRF treatment reduced the amount of back-fat accumulation in both male and female LY pigs.

TABLE 2

Relative gain in back-fat thickness in the LY pigs after plasmid injection.

|  | LY male | | LY female | |
|---|---|---|---|---|
|  | Control | pGHRF | Control | pGHRF |
| Relative gain in back-fat thickness | 51.3% | 34.9% | 24.2% | 5.1% |

The results of the examples show that treatment with the pGHRF gene is able to produce benefits in growth performance in both the mouse and pig. The gains in growth rates are comparable to those of GH treatments yet with a much more cost effective treatment regime. The quantity of DNA used per animal is at least 100 fold lower than that of growth hormone injection reported in the literature. Furthermore, the pig data shows that there are reductions in the amount of feed required as well as the thickness of back-fat. Therefore this invention will be beneficial to the livestock industry by enhancing feed efficiency and growth rate of livestock.

While the preferred embodiment of the present invention has been described in detail by the examples, it is apparent that modifications and adaptations of the present invention will occur to those skilled in the art. It is to be expressly understood, however, that such modifications and adaptations are within the scope of the present invention, as set forth in the following claims. Furthermore, the embodiments of the present invention shall not be interpreted to be restricted by the examples only.

SEQUENCE LISTING

<160> NUMBER OF SEQ ID NOS: 2

<210> SEQ ID NO 1
<211> LENGTH: 79
<212> TYPE: DNA
<213> ORGANISM: Sus scrofa

<400> SEQUENCE: 1
tacgccgacg ccatcttcac caacagctac aggaaggtgc ggccagctga gcgccaggaa    60
gctgctgcag gacatcatg    79

<210> SEQ ID NO 2
<211> LENGTH: 81
<212> TYPE: DNA
<213> ORGANISM: Sus scrofa

<400> SEQUENCE: 2
cgtctagatc acagcctcac cctggcgccc tgctcctggt tcctctcgcc ctgctgcctg    60
ctcatgatgt cctgcagcag c    81 back fat thickness as the animals aged, although those given the pGHRF expressing plasmid showed a reduced gain in back-fat. Female control pigs also showed a gradual gain in

What is claimed is:

1. A method of providing at least one of the effects of enhancing feed efficiencies, enhancing growth rates, or reducing fat accumulation in a porcine, said method comprising the step of administering an effective amount of a vector to the porcine to stimulate the production of growth hormone releasing factor (GHRF), wherein the vector comprises:

a promoter including an actin promoter for gene expression;

a DNA sequence encoding a GHRF signal peptide; and a porcine GHRF encoded DNA sequence comprising at least SEQ ID NO: 1 or SEQ ID NO: 2;

wherein the vector is administered through intramuscular injection, and the promoter and the DNA sequence encoding the GHRF signal peptide are operably linked to the porcine GHRF encoded DNA sequence.

2. The method as claimed in claim 1, wherein the actin promoter is a skeletal actin promoter.

3. The method as claimed in claim 1, wherein the vector further includes a 3' untranslated region of an alpha actin gene.

4. The method as claimed in claim 1, wherein the vector further includes a gene for antibiotic resistance.

5. The method as claimed in claim 1, wherein the actin promoter and the GHRF signal peptide are endogenous to the porcine.

6. The method as claimed in claim 1, wherein the vector is mixed with a carrier prior to said administering step.

7. The method as claimed in claim 1, wherein said effective amount of a vector is between the range of 1 to 100 µg per kg body weight of the porcine.

8. A vector to stimulate the production of growth hormone releasing factor (GHRF) to provide at least one of the effects of enhancing feed efficiencies, enhancing growth rates, or reducing fat accumulation in a porcine, wherein the vector comprises:

a promoter including an actin promoter for gene expression;

a DNA sequence encoding a GHRF signal peptide; and a porcine GHRF encoded DNA sequence comprising at least SEQ ID NO: 1 or SEQ ID NO: 2;

wherein the promoter and the DNA sequence encoding the GHRF signal peptide are operably linked to the porcine GHRF encoded DNA sequence.

9. The vector as claimed in claim 8, wherein the actin promoter is a skeletal actin promoter.

10. The vector as claimed in claim 8, wherein the vector further includes a 3' untranslated region of an alpha actin gene.

11. The vector as claimed in claim 8, wherein vector further includes a gene for antibiotic resistance.

12. The vector as claimed in claim 8, wherein the actin promoter and the GHRF signal peptide are endogenous to the porcine.

13. A method of manufacturing a vector to provide at least one of the effects of enhancing feed efficiencies, enhancing growth rates, or reducing fat accumulation in a porcine, said method comprising the steps of:

joining a promoter including an actin promoter for gene expression, to a DNA encoding a growth hormone releasing factor (GHRF) signal peptide; and joining a porcine GHRF encoded DNA sequence comprising at least SEQ ID NO: 1 or SEQ ID NO: 2, to the DNA sequence encoding the GHRF signal peptide to form the vector.

14. The method as claimed in claim 13, wherein the actin promoter is a skeletal actin promoter.

15. The method as claimed in claim 13 further comprising the step of joining a 3' untranslated region of an alpha actin gene to the vector.

16. The method as claimed in claim 15 further comprising the step of joining a gene for ampicillin resistance to the porcine GHRF encoded DNA sequence.

17. The method as claimed in claim 16, wherein the DNA sequences of the vector are joined together sequentially in the following order: the DNA sequence encoding the promoter; the DNA sequence encoding the GHRF signal peptide; the porcine GHRF encoded DNA sequence; the 3' untranslated region of an alpha actin gene; the gene for antibiotic resistance.

18. The method as claimed in claim 13, wherein the DNA sequences of the vector are joined by ligation.

19. The method as claimed in claim 13, wherein the actin promoter and the GHRF signal peptide are endogenous to the porcine.

* * * * *